US010292964B2

(12) United States Patent
Heaton et al.

(10) Patent No.: US 10,292,964 B2
(45) Date of Patent: *May 21, 2019

(54) COMPOSITIONS FOR INCREASING HUMAN GROWTH HORMONE LEVELS

(71) Applicant: Quality IP Holdings, LLC, Carson City, NV (US)

(72) Inventors: Amy L. Heaton, Salt Lake City, UT (US); Mitchell K. Friedlander, Salt Lake City, UT (US); Dennis Gay, Salt Lake City, UT (US)

(73) Assignee: Quality IP Holdings, LLC, Salt Lake City (*) Notice: Subject to any disclaimer, the term of this patent is extended or adjusted under 35 U.S.C. 154(b) by 0 days.

This patent is subject to a terminal disclaimer.

(21) Appl. No.: 14/271,242

(22) Filed: May 6, 2014

(65) Prior Publication Data

US 2014/0242201 A1 Aug. 28, 2014

Related U.S. Application Data

(63) Continuation of application No. 13/623,117, filed on Sep. 20, 2012, now Pat. No. 8,715,752.

(51) Int. Cl.

| | |
|---|---|
| *A61K 36/55* | (2006.01) |
| *A61K 36/00* | (2006.01) |
| *A61K 47/00* | (2006.01) |
| *A61K 9/14* | (2006.01) |
| *A61K 9/00* | (2006.01) |
| *A61K 31/4015* | (2006.01) |
| *A61K 31/401* | (2006.01) |
| *A61K 36/538* | (2006.01) |
| *A61K 31/198* | (2006.01) |

(52) U.S. Cl.
CPC ........ *A61K 31/4015* (2013.01); *A61K 31/198* (2013.01); *A61K 31/401* (2013.01); *A61K 36/538* (2013.01)

(58) Field of Classification Search
CPC ... A61K 31/198; A61K 31/195; A61K 31/401
See application file for complete search history.

(56) References Cited

U.S. PATENT DOCUMENTS

| | | |
|---|---|---|
| 4,224,316 A | 9/1980 | Momany |
| 6,071,926 A | 6/2000 | Van Cauter et al. |
| 6,346,264 B1 | 2/2002 | White |
| 6,368,617 B1 | 4/2002 | Hastings et al. |
| 6,517,832 B1 | 2/2003 | Marrongelle et al. |
| 6,974,841 B1 | 12/2005 | Rapisarda |
| 7,790,683 B2 | 9/2010 | Grasso et al. |
| 8,551,542 B1 | 10/2013 | Heaton et al. |
| 8,722,114 B2 | 5/2014 | Heaton et al. |
| 8,722,115 B2 | 5/2014 | Heaton et al. |
| 8,734,864 B2 | 5/2014 | Heaton et al. |
| 8,747,921 B2 | 6/2014 | Heaton et al. |
| 8,747,922 B2 | 6/2014 | Heaton et al. |
| 8,747,923 B2 | 6/2014 | Heaton et al. |
| 8,765,195 B2 | 7/2014 | Heaton et al. |
| 2002/0165343 A1 | 11/2002 | Martinez et al. |
| 2003/0068309 A1 | 4/2003 | De Simone |
| 2004/0063608 A1 | 4/2004 | Mowrey et al. |
| 2004/0122234 A1 | 6/2004 | Hauser et al. |
| 2007/0286909 A1 | 12/2007 | Smith et al. |
| 2008/0050777 A1 | 2/2008 | Buechler et al. |
| 2010/0047364 A1 | 2/2010 | Moneymaker et al. |
| 2010/0186121 A1 | 7/2010 | Unkefer et al. |
| 2011/0052754 A1 | 3/2011 | Foley |
| 2011/0081329 A1 | 4/2011 | Smith et al. |
| 2014/0079822 A1 | 3/2014 | Heaton et al. |
| 2014/0079823 A1 | 3/2014 | Heaton et al. |
| 2014/0079830 A1 | 3/2014 | Heaton et al. |
| 2014/0079832 A1 | 3/2014 | Heaton et al. |
| 2014/0080887 A1 | 3/2014 | Heaton et al. |
| 2014/0080888 A1 | 3/2014 | Heaton et al. |

FOREIGN PATENT DOCUMENTS

| | | |
|---|---|---|
| CN | 1243745 A | 2/2000 |
| GB | 9822333 | 12/1998 |
| KR | 1020000000757 A | 1/2000 |
| RU | 2429001 C1 | 9/2011 |
| WO | 9528854 A1 | 11/1995 |
| WO | 2004112511 A2 | 12/2004 |
| WO | 2007095618 A3 | 10/2007 |

OTHER PUBLICATIONS

Reid et al. (1994) J.Clin. Invest. 94: 2468-2474.*
Website document entitled Growth Hormone: Amino Acids as GH Secretogues (available at http://www.vrp.com/amino-acids/growth-hormone-amino-acids-as-gh-secretogues-a-review-of-the-literature?utm-source=RSStwitterfeed&utm-medium=twitter). Downloaded Apr. 8, 2013.*
Fung et al. (2002) J. Clin. Pharmacol. 42: 30-36.*
Alba-Roth et al.; Arginine Stimulates Growth Hormone Secretion by Suppressing Endogenous Somatostatin Secretion; Journal of Clinical Endocrinology and Metabolism, vol. 67, No. 6, 1988; 1186-1189.
Albert et al.; Low-Dose Recombinant Human Growth Hormone as Adjuvant Therapy of Lifestyle Modifications in the Management of Obesity; Journal of Clinical Endocrinology & Metabolism 89(2) 695-704; 2004.
Bae, O.; "A Chinese medicinal composition for stimulating growth hormone", KR 2000/000757 A, 2000, Abstract Only.
Bernardi et al.; Somatotropic axis and body weight in pre-menopausal and post-menopausal women: evidence for a neuroendocrine derangement, in absence of changes of insulin-like growth factor binding protein concentrations; Human Reproduction vol. 12, No. 2 pp. 279-287, 1998.
Bidlingmaier et al.; Growth Hormone; Handbook of Experimental Pharmacology 195; 2010; pp. 187-200.
Bjorntorp, et al.; Hypothalamic Origin of the Metabolic Syndrome X; Annals New York Academy of Sciences, pp. 297-307; 1999.

(Continued)

*Primary Examiner* — Christopher R Tate
*Assistant Examiner* — Russell G Fiebig
(74) *Attorney, Agent, or Firm* — Magleby Cataxinos & Greenwood

(57) ABSTRACT

Embodiments of the invention generally relate to supplements for increasing human growth hormone (hGH) levels in healthy human beings.

6 Claims, 1 Drawing Sheet

(56) References Cited

OTHER PUBLICATIONS

Bjorntorp, P.; Do Stress reactions cause abdominal obesity and comorbidities?; The International Association for the Study of Obesity, Obesity reviews; 2 73-85; 2001.

Bjorntorp, P.; The regulation of adipose tissue distribution in humans; International Journal of Obesity (1996) 20, 191-302.

Blackman et al.; Growth Hormone and Sex Steroid Administration in Healthy Aged Women and Men a Randomized Controlled Trial; JAMA, Nov. 12, 2002—vol. 288, No. 18; pp. 2282-2292.

Boger, R. H., "The Pharmacodynamics of L-Arginine1-3", The Journal of Nutrition: 6th Amino Acid Assessment Workshop, 2007, pp. 1650S-1655S, vol. 137, American Society for Nutrition.

Bredella, et al.; Peak Growth Hormone-Releasing Hormone-Arginine-Stimulated Growth Hormone is Inversely Associated with Intramyocellular and Intrahepatic Lipid Content in Premenopausal Women with Obesity; J. Clin Endrocrinol Metab. Oct. 2009; 94(10): 3995-4002.

Carli et al.; Changes in the exercise-induced hormone response to branched chain amino acid administration; Eru. J. Appl. Physiology (1992) 64:272-277.

Chowen et al.; The regulation of GH secretion by sex steroids; European Journal of Endocrinology, 2004, pp. U95-U100, vol. 151, Society of the European Journal of Endocrinology.

Chromiak et al.; Use of Amino Acids as Growth Hormone-Releasing Agents by Athletes; Nutrition 18:657-661, 2002.

Collier, S. R. et al., "Growth hormone responses to varying doses of oral arginine", Growth Hormone & IGF Research, 2005, vol. 15, pp. 136-139.

Cooper et al.; "Subclinical thyroid disease," Jan. 23, 2012, 13 pages.

Corpas et al.; Human Growth Hormone and Human Aging; Endocrine Reviews, vol. 14, No. 1; 1993; pp. 20-39.

Corpas et al.; Oral Arginine-Lysine Does not Increase Growth Hormone or Insulin-like Growth Factor-I in Old Men; Journal of Gerontology: 1993, vol. 48, No. 4, M128-M133.

Devesa et al.; "The Role of Sexual Steroids in the Modulation of Growth Hormone (GH) Secretion in Humans," J. Steroid Biochem. Molec. Biol., 1991,vol. 40—No. 1-3, pp. 165-173.

Ding et al.; Novel serum protein biomarkers indicative of growth hormone doping in healthy human subjects; Preteomics Nov. 2011, 3565-3571.

"External Wind", <http://www.tcvmherbal.com/JTDocs/Flyers/External%20Wind.pdf>, Downloaded from website Oct. 22, 2013, Jing Tang, 2 pages.

Farr et al.; "The antioxidants α-lipoic acid and N-acetylcysteine reverse memory impairment and brain oxidative stress in aged SAMP8 mice," Journal of Neurochemistry, 2003, vol. 84, pp. 1173-1183.

Fogelholm et al. Low-Dose Amino Acid Supplementation: No Effects on Serum Human Growth Hormone and Insulin in Male Weightlifters; International Journal of Sport Nutrition, Mar. 1993, 290-297.

Fung, et al; "Schizonepeta tenuifolia: Chemistry, Pharmacology, and Clinical Applications," J. Clin. Pharmacal., 2002, vol. 42, pp. 30-36.

Gasco et al.; "Retesting the childhood-onset GH-deficient patient," European Journal of Endocrinology, vol. 159, 2008, pp. S45-S52.

Goto et al.; "Growth Hormone Receptor Antagonist Treatment Reduces Exercise Performance in Young Males", Sep. 2009, J Clin Endocrinol Metab, 94(9), pp. 3265-3272.

Gourmelen et al., Effet du chlorhydrate d'ornithine sur le taux plamatique de l'hormone de croissance (HGH); Annels D'Endocrinologie; pp. 526-528; 1972.

Grioli et al. "Pyroglutamic acid improves the age associated memory impairment," citation and abstract from Pyroglutamate, Jun. 13, 2002, Retrieved from the Internet on Apr. 9, 2013. Retrieved from: <http://web.archive.org/web/20020613031716/http://www.raysahelian.com/pyroglutamate.html>, 1 page.

Grunfeld et al.; "The Acute Effects of Human Growth Hormone Administration on Thyroid Function in Normal Men," Journal of Clinical Endocrinology and Metabolism, 1988, vol. 67—No. 5, pp. 1111-1114.

Hansen et al.; Effects of 2 wk of GH administration on 24-h indirect calorimetry in young, healthy, lean men; Am. J. Physiol Endocrinol Metab 289: E1030-E1038, 2005.

Hayes et al.; Recombinant Human Growth Hormone and Recombinant Human Insulin-Like Growth Factor I Diminish the Cataboloic Effects of Hypogonadism in Man: Metabolic and Molecular Effects; The Journal of Clinical Endocrinology & Metabolism; vol. 86, No. 5; 2001.

Hersch et al.; Growth hormone (GH)-releasing hormone and GH secretagogues in normal aging: Fountain of Youth or Pool of Tantalus?; Clinical Interventions in Aging 2008:3(1) 121-129.

Ho et al.; "The Pharmacokinetics, Safety and Endocrine Effects of Authentic Biosynthetic Human Growth Hormone in Normal Subjects", Clinical Endocrinology, 1989, vol. 30, pp. 335-345.

Iranmanesh et al., Age and Relative Adiposity are Specific Negative Determinants of the Frequency and Amplitude of Growth Hormone (GH) Secretory Bursts and the Half-Life of Endogenous GH in Healthy Men; Journal of Clinical Endocrinology and Metabolism; vol. 73, No. 5; pp. 1081-1088.

Isidori et al.; A Study of growth hormone release in man after oral administration of amino acids; Current Medical Research and Opinion; vol. 7, No. 7, 1981; pp. 475-481.

Karlsson et al.; Effects of growth hormone treatment on the leptin system and on energy expenditure in abdominally obese men; European Journal of Endocrinology (1998) 138 408-414.

Kim et al.; "Anti-Inflammatory Activity of Schizonepeta tenuifolia through the Inhibition of MAPK Phosphorylation in Mouse Peritoneal Macrophages," The American Journal of Chinese Medicine, vol. 36—No. 6, pp. 1145-1158.

King, J.; "What is L-Arginine HCL?", <http://www.livestrong.com/article/464027-what-is-l-arginine-hcl/>, Jun. 5, 2011, 6 pages.

Kraemer et al.; Chronic Resistance training in women potentiates growth hormone in vivo bioactivity: characterization of molecular mass variants; Am. J. Physiol Endocrinol Metab 291: E1177-E1187, 2006.

Lambert et al.; Failure of Commercial Oral Amino Acid Supplements to Increase Serum Growth Hormone Concentrations in Male Body-Builders; International Journal of Sport Nutrition, Mar. 1993, 298-305.

Leelarungrayub et al.; "N-Acetylcysteine Supplementation Controls Total Antioxidant Capacity, Creatine Kinase, Lactate, and Tumor Necrotic Factor-Alpha against Oxidative Stress Induced by Graded Exercise in Sedentary Men," Oxidative Medicine and Cellular Longevity. vol. 2011, Article ID 329643, 7 pages.

Legakis et al.; Human Galanin Secretion is Increased Upon Normal Exercise Test in Middle-Age Individuals; Endocrine Research 26(3), 357-365 (2000).

"L-Lysine," <http://www.ironmagazineforums.com/threads/149021-L-Lysine>, Retrieved from the Internet on: Jul. 15, 2014, 7 pages.

Maccario et al.; Relationships between IFG-I and age, gender, body mass, fat distribution, metabolic and hormonal variables in obese patients; International Journal of Obesity (1999) 23, 612-618.

Maggi et al.; "Hormonal Causes of Male Sexual Dysfunctions and Their Management (Hyperprolactinemia, Thyroid Disorders, GH Disorders, and DHEA)," International Society for Sexual Medicine, 2012, 9 pages.

Makimura et al.; The relationship between reduced testosterone, stimulated growth hormone secretion and increased carotid inimamedia thickness in obese men; Clin Endocrinol (Oxf). Nov. 2010; 73(5): 622-629.

Mayo Clinic Staff; "Post-traumatic stress disorder (PTSD)," <http://www.mayoclinic.org/diseases-conditions/post-traumatic-stress-disorder/basicsidefinition/con-20022540>, Apr. 15, 2014.

Menagh et al.; Growth Hormone Regulates the Balance Between Bone Formation and Bone Marrow Adiposity; JBMR; vol. 25, No. 4, Apr. 2010, pp. 757-768.

Merimee et al.; Arginine-Initiated Release of Human Growth Hormone; The New England Journal of Medicine; Jun. 26, 1969; pp. 1434-1438.

Millea, P. J.; "N-Acetylcysteine: Multiple Clinical Applications," American Family Physician, Aug. 1, 2009, vol. 80—No. 3, pp. 265-269.

(56) References Cited

OTHER PUBLICATIONS

Moller et al.; "Effects of Growth Hormone Administration on Fuel Oxidation and Thyroid Function in Normal Man," Metabolism, vol. 41—No. 7, Jul. 1992, pp. 728-731.
Nindl et al.; Growth hormone pulsatility profile characteristics following acute heavy resistance exercise; J. Appl Physiol 91: 163-172, 2001.
O'Connor et al.; Interrelationships of Spontaneous Growth Hormone Axis Activity, Body Fat, and Serum Lipids in Healthy Elderly Women and Men; Metabolism, vol. 48, No. 11 (Nov. 1999): pp. 1424-1431.
Oliveira, et al.; "Free Amino Acids of Tronchuda Cabbage (*Brassica oleracea* L. var. *costata* DC): Influence of Leaf Position (Internal or External) and Collection time", Journal of Agricultural and Food Chemistry, 2008, vol. 56, pp. 5216-5221.
Papadakis et al.; Effect of growth hormone replacement on wound healing in healthy older men; Would Repair and Regeneration Oct.-Dec. 1996; pp. 421-425.
Papadakis et al.; Growth Hormone Replacement in Healthy Older Men Improves Body Composition but Not Functional Ability; Ann Intern Med. 1996; 124-: 708-716.
Pasquali et al.; Hormones and pathophysiology of obesity; Hormones and Obesity; 2001 pp. 9-20.
Pavel et al.; "Impact of Growth Hormone on Central Nervous Activity, Vigilance, and Tiredness after Short-Term Therapy in Growth Hormone-Deficient Adults," Horm. Metab. Res., 2003, vol. 35, pp. 114-119.
PCT Search Report for International application No. PCT/US2013/060669, dated Jan. 9, 2014, 3 pages.
Pelsers et al.; Influence of Gender in Growth Hormone Status in Adults: Role of Urinary Growth Hormone; Clinical Chemistry 45, No. 3, 1999, pp. 443-444.
Perry, Horace M. III; The Endocrinology of Aging; Clinical Chemistry 45:8(B); 1369-1376 (1999).
Pradines-Figueres et al.; "Transcriptional control of the expression of lipoprotein lipase gene by growth hormone in preadipocyte Ob1771 cells," Journal of Lipid Research, vol. 31, 1990, pp. 1283-1291.
Pryor, et al.; "Growth Hormone: Amino Acids as GH secretagogues," <http://www.vrp.com/amino-acids/amino-acids/growth-hormone-amino-acids-as-gh-secretagogues-a-review-of-the-literature>, Retrieved Jul. 16, 2014, 5 pages.
Reid et al.; "N-Acetylcysteine Inhibts Muscle Fatigue in Humans," J. Clin. Invest., vol. 94, Dec. 1994, pp. 2468-2474.
Roddick, J.; "Sleep Disorders," <http://www.healthline.com/health/sleep/disorders#Overview 1>, Retrieved from the Internet on Jul. 16, 2014, 3 pages.
Rubin et al.; New anabolic therapies in osteoporosis; Current Opinon in Reeumatology 2002, 14:433-440.
Rudman et al.; "The Short Child with Subnormal Plasma Somatomedin C1," Pediatric Research, vol. 19—No. 10, 1985, pp. 975-980.
Rudman et al.; Effects of Human Growth Hormone in Men over 60 Years Old; The New England Journal of Medicine; vol. 323, Jul. 5, 1990; 6 pages.
Russell et al.; "Free Triiodothyronine has a distinct circadian rhythm that is delayed but parallels thyrotropin levels," J. Clin Endocrin Metab., Mar. 25, 2008, 22 pages.
Sahley, B J. "Amino Acid Brain Boosters" <http://www.teenlinkusa.com/aminoacids2.html>, Retrieved on Jul. 16, 2014, 4 pages.
Salomon et al.; "The Effects of Treatment with Recombinant Human Growth Hormone on Body Composition and Metabolism in Adults with Growth Hormone Deficiency," New England Journal of Medicine, Dec. 28, 1998, vol. 321—No. 26, pp. 1797-1803.
"Schizonepeta Tenuifolia," <http://examine.com/supplements/Schizonepeta+tenuifolia/>, Sep. 30, 2013, 12 pages.
Schwartz et al., "Hormone Replacement Therapy in the Geriatric Patient: Current State of the Evidence and Questions for the Future. Estrogen, Progesterone, Testosterone, and Thyroid Hormone Augmentation in Geriatric Clinical Practice: Part 1," Clin Geriatr Med vol. 27, 2011, pp. 541-559.
Schwartz et al., "Hormone Replacement Therapy in the Geriatric Patient: Current State of the Evidence and Questions for the Future. Estrogen, Progesterone, Testosterone, and Thyroid Hormone Augmentation in Geriatric Clinical Practice: Part 2," Clin Geriatr Med, vol. 27, 2011, pp. 561-575.
Sen et al.; "Exercise-induced oxidative stress: glutathione supplementation and deficiency," J. Appl. Physiol., vol. 77, 1994, pp. 2177-2187.
Sen et al.; "Oxidative stress after human exercise: effect of N-acetylcysteine supplementation," J. Appl. Physiol., vol. 76, 1994, pp. 2570-2577.
Sen, C. K.; "Glutathione homeostasis in response to exercise training and nutritional supplements," 1999, Molecular and Cellular Biochemistry, vol. 196, pp. 31-42.
Sevigny et al.; "Growth hormone secretagogue MK-677: No clinical effect on AD progression in a randomized trial," American Academy of Neurology, 2008, vol. 71, pp. 1702-1708.
Silber et al.; "Growth and Maintenance of Dogs Fed Amino Acids as the Source of Dietary Nitrogen," The Journal of Nutrition, Oct. 11, 1948, pp. 429-441.
Smith et al.; "Sleep Disorders and Sleeping Problems," <http://www.helpguide.org/life/sleep_disorders.htm>, Jun. 2014, Helpguide.org, 7 pages.
Su et al.; Insulin-like growth factor 1 and hair growth; 1999 Dermatology Online Journal; 20 pages.
Suminski et al.; Acute Effect of Amino Acid Ingestion and Resistance Exercise on Plasma Growth Hormone Concentration in Young Men; International Journal of Sport Nutrition, Jul. 1997, 48-60.
Tarantini et al.; "Serum ghrelin levels in growth hormone-sufficient and growth hormone-deficient patients during growth hormone-releasing hormone plus arginine test," J. Endocrinol. Invest. vol. 32, pp. 335-337, 2009.
Tavakkolizadeh et al.; "Effect of Growth Hormone on Intestinal NA+/Glucose Cotransporter Activity," Journal of Parenteral and Enteral Nutrition, vol. 25, No. 1, Mar. 2000, pp. 18-22.
Topo et al.; "The role and molecular mechanism of D-aspartic acid in the release and synthesis of LH and testosterone in humans and rats," Reproductive Biology and Endocrinology, Oct. 27, 2009, 11 pages.
Twickler et al.; Adult-Onset Growth Hormone Deficiency: Relation of Postprandial Dyslipidemia to Premature Atherosclerosis; The Journal of Clinical Endocrinology & Metabolism 88(6): 2479-2488.
Van Cauter et al.; "Metabolic consequences of sleep and sleep loss," Sleep Medicine 9 Suppl. 1, 2008, pp. S23-S28.
Van Liempt et al.; "Decreased nocturnal growth hormone secretion and sleep fragmentation in combat-related posttraumatic stress disorder; potential predictors of impaired memory consolidation," Psychoneuroendocrinology, 2011, vol. 36, pp. 1361-1369.
Vance, Mary L.; Growth Hormone for the Elderly?; The New England Journal of Medicine; Jul. 5, 1990; pp. 52-54.
Vermeulen et al., "Testosterone, body composition and aging," J. Endocrinol. Invest., vol. 22, pp. 110-116, 1999.
Weikel et al.; "Ghrelin promotes slow-wave sleep in humans," Am J. Physiol Endocrinol Metab, vol. 284, pp. E407-E415, 2003.
Weizman et al.; "Impact of the Gulf War on the Anxiety, Cortisol, and Growth Hormone Levels of Israeli Civilians," Am J. Psychiatry, vol. 151—No. 1, Jan. 1994, pp. 71-75.
Welbourne, T. C.; "Increased plasma bicarbonate and growth hormone after an oral glutamine load 81-3," The American Journal of Clinical Nutrition, 1995, vol. 61, pp. 1058-1061.
White et al.; Effects of an Oral Growth Hormone Secretagogue in Older Adults; J. Clin Endocrin Metab.; 2009; 29 pages.
Yen et al.; "Aging and the Adrenal Cortex," Experimental Gerontology, vol. 33, Nos. 7/8, pp. 897-910, 1998.
Yuen et al.; "Is Lack of Recombinant Growth Hormone (GH)-Releasing Hormone in the United States a Setback or Time to Consider Glucagon Testing for Adult GH Deficiency?", J. Clin, Endocrinol Metab, Aug. 2009, vol. 94—No. 8, pp. 2702-2707.
Zouboulis et al.; Intrinsische Hautalterung; Eine kritische Bewertung der Rolle der Hormone; Hautarzt 2003 54: 825-832.

(56) References Cited

OTHER PUBLICATIONS

Brigitte Mars. Internet Publication Date: Mar. 1, 2009 [Retrieved from the Internet on: Jul. 3, 2014]. Retrieved from: <URL: http://brigittemars.com/articles/herbal-natural-remedies/treating-headaches-naturally/>.

Anonymous, "Dr. Oz Human Growth Hormone HGH the Pursuit of Youth and Beauty," Oct. 13, 2011, retrieved from the internet: URL:http://healthybodydaily.com/dr-oz-in-case-you-missed-it/dr-oz=hgh-human-growth-hormone (retrieved on Sep. 15, 2014).

Anonymous, "Animal Outreach," Aug. 18, 2012, retrieved from the internet: URL: http://aninnal-outreach.org/2012/08 (retrieved on Sep. 15, 2014).

Extended European Search Report for application No. 13823912.4-1464/2744490, based on PCT/US2013060645, 4 pages.

"MedlinePlus: L-arginine". Internet Archive Datae:Oct. 5, 2010 [Retrieved from the Internet on: Jul. 31, 2014]. Retrieved from: <URL: http://www.nlm.nih.gov/medlineplus/druginfo/natural/875.html>.

\* cited by examiner

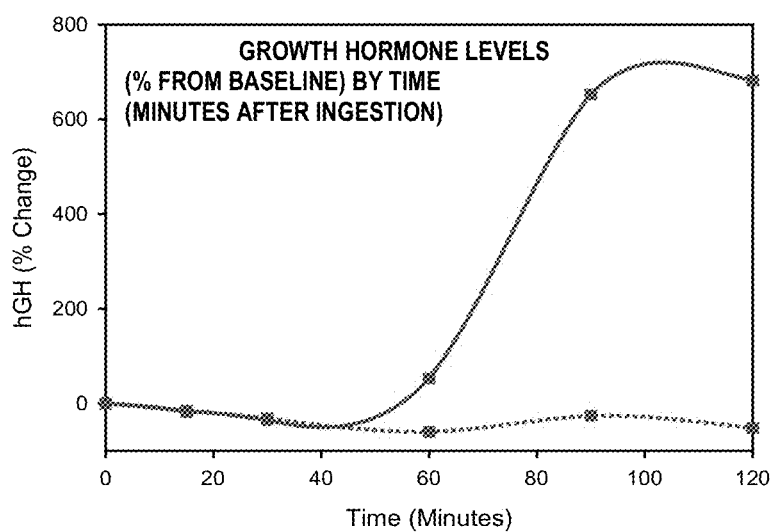

COMPOSITIONS FOR INCREASING HUMAN GROWTH HORMONE LEVELS

CROSS-REFERENCE TO RELATED APPLICATION

This application is a continuation of U.S. patent application Ser. No. 13/623,117, filed Sep. 20, 2012, now U.S. Pat. No. 8,715,752, issued on May 6, 2014, the disclosure of which is hereby incorporated herein in its entirety by this reference.

TECHNICAL FIELD

Embodiments of the invention generally relate to supplements for increasing human growth hormone (hGH) levels in healthy human beings.

BACKGROUND

The primary biological function of hGH includes stimulating growth, cell repair and regeneration. Once the primary growth period of adolescence concludes, the primary function of hGH in adulthood becomes that of cell regeneration and repair, helping regenerate skin, bones, heart, lungs, liver and kidneys to their optimal, youthful cell levels. As is the case with many of our other hormones or their pre-cursors, such as testosterone, oestrogen, progesterone, DHEA and melatonin, hGH levels decline with age. Therapeutically, many of these hormones can be replaced to offset some of the effects of aging such as menopausal symptoms in women or erectile dysfunction in men. The human body, like every other living entity, works on daily, or circadian, as well as monthly and annual rhythms. Daily growth hormone secretion diminishes with age with roughly half the levels at age forty that we had when we were twenty, and about one-third of those youthful levels at age sixty. In some sixty-year olds, the levels are as low as 25% of the hGH levels in a twenty-year old. Symptoms of aging include loss of muscle, increase of fat, decreased physical mobility, decreased energy levels and as a result, diminished socialization, diminished healing ability and an increased risk of cardiovascular disease and decreased life expectancy. Low hGH levels are associated with the aging process and early onset of disease. For example, Rosen and Bengtsson noted an increased death rate from cardiovascular disease in hGH deficient patients (Rosen, T., Bengtsson, B. A., Lancet 336 (1990): 285-2880).

Until recently human growth hormone (hereinafter alternatively referred to as hGH) was available only in expensive injectable forms, and benefits from the restoration of hGH levels available only to those with the ability to pay. Most recently substances that can trigger the release of human growth hormone from an individual's own anterior pituitary gland have become available. These are generically referred to as secretagogues. Secretagogues have the ability to restore hGH levels, potentially to the levels found in youth. See for reference the book entitled "Grow Young With hGH" by Dr. Ronald Klatz, President of the American Academy of Anti-Aging, published in 1997 by Harper Collins.

HGH-deficient adults have marked reductions in lean body mass, and within months of hGH treatment, gains in lean body mass, skin thickness and muscle mass are observed. (Cuneo R C et al. J Appl Physiol 1991; 70:695-700; Cuneo R C et al. J Appl Physiol 1991; 70:688-694; Rudman D et al. N Engl J Med 1969; 280:1434-1438).

It is well-established that intravenous (IV) administration of some amino acids results in significant hGH secretion. Intravenous infusion of 183 mg of arginine/kg body weight in females increased hGH levels>20-fold and 30 g of arginine elevated serum hGH levels 8.6 fold in males (Merimee T J et al. N Engl J Med 1969; 280:1434-1438; Alba-Roth J et al. J Clin Endocrinol Metab 1988; 67:1186-1189). Other amino acids, such as methionine, phenylalanine, lysine, histidine, and ornithine have also led to marked increases in hGH (Alba-Roth, Muller, Schopohl, & von Werder, 1988; Chromiak & Antonio, 2002; Gourmelen, M., M. Donnadieu, et al. (1972) Ann Endocrinol (Paris) 33(5): 526-528).

Given the difficulties in IV administration of amino acids for widespread use, interest in elucidating the hGH response to oral amino acid supplements prompted testing of such supplements containing mainly arginine, lysine and ornithine at varying amounts. Yet the pronounced variability in results among these studies, which differed in aspects including subject population, supplement composition, and dosage methodologies, make clear the complexities involved in the design of an effective supplement for supporting hGH levels in the general public. (Suminski R R et al. Int J Sport Nutr 1997; 7:48-60; Lambert M I et al. Int J Sport Nutr 1993; 3:298-305; Corpas E et al. J Gerontol 1993; 48:M128-M133; Isidori A et al. Curr Med Res Opin 1981; 7:475-481; Fogelholm G M et al. Int J Sport Nutr 1993; 3:290-297; Chromiak J A, Antonio J. Nutrition 2002 July; 18(7-8):657-61).

Thus determination of an effective and safe oral functional blend that stimulates hGH secretion in the general population is important to determine since athletes, entertainers and now the general public seek effective hGH support supplements and understand hGH to have rejuvenating properties.

Indeed, once partial to athletes and entertainers, the desire for effective supplements to provoke growth hormone (hGH) increases now extends to the general public. Not only do they have a goal of building lean tissue and reducing fat, but also in improving skin quality and other rejuvenating qualities that hGH is understood to provide. Despite proceeding literature on oral amino acids for use in stimulating hGH, evidence for an optimized oral amino acid-containing blend able to stimulate hGH in the general public including both men and women of a wide age range is not clear.

It would be desirable to provide a nutritional supplement for elevating hGH release, in particular an amino acid-containing composition that is well tolerated having the result of increasing or elevating hGH release in those individuals whose hGH release rates have slowed as a function of increasing age or that have normal hGH levels but desire higher hGH levels. Although some existing nutritional supplements claim to impact the production of natural human growth hormone, there is a need for an improved nutritional supplement that efficiently enhances the production and effect of natural human growth hormone in the general population.

BRIEF SUMMARY OF THE INVENTION

The present invention is a nutritional supplement. It is a novel amino acid-containing secretagogue composition, which, taken orally, stimulates the pituitary gland to increase serum levels of hGH.

A particular embodiment of the present disclosure relates to an oral nutritional supplement that includes the amino acids l-lysine, l-arginine, oxo-proline, and one of either cysteine or glutamine. The amino acids may be delivered as non-toxic salts thereof, effective complexes thereof, stable chelates thereof, active esters thereof, functional derivatives thereof, and mixtures thereof which are effective to increase hGH levels in the general population.

Another particular embodiment relates to an oral nutritional supplement that consists essentially of l-lysine HCl, l-arginine HCl, oxo-proline, N-acetyl-l-cysteine, l-glutamine, and schizonepeta (aerial parts) powder.

BRIEF DESCRIPTION OF THE FIGURES

FIG. 1 shows growth hormone levels after supplement administration compared to a placebo.

DETAILED DESCRIPTION OF THE INVENTION

The present invention relates to a nutritional supplement for use by a human being. The nutritional supplement is an amino acid-containing secretagogue composition, which, taken orally, stimulates the pituitary gland to increase serum levels of hGH. Increased levels of hGH may result in inhibition of insulin depression, inhibition of hyperglycaemia and increase in insulin effectiveness, enhancement of fat conversion, lowering of cholesterol, and normalization of lipid balance. The supplement of the present invention works as a dietary supplement by assisting the body's own ability to secrete hGH naturally in a manner that is safe and effective, as well as being affordable.

A particular embodiment of the present disclosure relates to an oral nutritional supplement that includes l-lysine, l-arginine, oxo-proline, and one of either cysteine or glutamine. The supplement may additionally include both cysteine and glutamine and/or schizonepeta powder. In particular embodiments, a functional dosage includes the l-arginine at a level between 0.1-6 mmol and the oxo-proline between 0.1-8 mmol, and/or the 1-lysine in an amount between 0.1-12 mmol. The cysteine and/or glutamine may be contained at a level between 0.001-6 mmol. In another particular embodiment, a functional dosage includes the l-arginine HCl at a level between 2.5-4.5 mmol and the oxo-proline between 4-6 mmol, and/or the l-lysine HCl in an amount between 7-9 mmol. The cysteine and/or glutamine may be contained at a level between 0.001-0.5 mmol. The cysteine can be n-acetyl L-cysteine and the glutamine may be l-glutamine. The amino acids may be delivered as non-toxic salts thereof, effective complexes thereof, stable chelates thereof, active esters thereof, functional derivatives thereof, and mixtures thereof which are effective to increase hGH levels in the general population. The nutritional supplement may be present in an amount of 2.9 grams. The nutritional supplement may be in any acceptable and known oral formulation, such as powder, tablet, capsule, liquid, or wafer form.

Another particular embodiment relates to an oral nutritional supplement that consists essentially of l-lysine HCl, l-arginine HCl, oxo-proline, N-acetyl-l-cysteine, l-glutamine, and schizonepeta (aerial parts) powder. In particular embodiments, a functional dosage includes the l-arginine HCl at a level between 0.1-6 mmol and the oxo-proline between 0.1-8 mmol, and/or the l-lysine HCl in an amount between 0.1-12 mmol. The n-acetyl L-cysteine and/or l-glutamine may be contained at a level between 0.001-6 mmol. In another particular embodiment, a functional dosage includes the l-arginine HCl at a level between 2.5-4.5 mmol and the oxo-proline between 4-6 mmol, and/or the l-lysine HCl in an amount between 7-9 mmol. The n-acetyl L-cysteine and/or l-glutamine may be contained at a level between 0.001-0.5 mmol. The nutritional supplement may be in any acceptable and known oral formulation, such as powder, tablet, capsule, liquid, or wafer form.

Other embodiments are drawn to methods of increasing human growth hormone in humans that include orally administering the disclosed nutritional supplement to a healthy human being. As used herein, "healthy human being" means a human being without any physiological deficiency in hGH independent of age. Particular embodiments of the invention relate to oral administration of the disclosed nutritional supplement to a human that is at least 30 years old. The nutritional supplement may be administered from one to three times daily or, alternatively, may be administered every other day, or may be administered once a week. In particular embodiments, the nutritional supplement may be administered on an empty stomach.

In accordance with the "consist essentially of" and "consisting essentially of" language, the nutritional supplement of the third embodiments is essentially limited to the aforementioned ingredients and does not include any additional active ingredients intended to add nutritional content (e.g., vitamins, minerals, etc.), but may include additional ingredients not intended to add nutritional content such as ingredients intended to fulfill a non-nutritional purpose (e.g., coloring, fillers, flavoring, an ingredient for maintaining the structural form, etc.).

Each ingredient of the nutritional supplement of the present invention may be prepared in accordance with any method known to one of ordinary skill in the art. Alternatively, each ingredient may be obtained in a fully prepared from a commercially available source.

The nutritional supplement of the present invention may be in any suitable oral administration form, including but not limited to: a chewable form, a liquid form, a spray form, a capsule form, a suppository form, dissolvable wafer, and a powder form.

Irrespective of the structural form of the nutritional supplement, the ingredients of the nutritional supplement may be distributed homogeneously or non-homogeneously within the nutritional supplement.

The nutritional supplement of the present invention may be ingested on a regular basis, such as a daily or weekly intake at a dosage tailored to an individual's needs; i.e., the nutritional supplement is to be taken regularly as multiples (1×, 2×, etc.) of the structural units (pills, tablets, capsules, liquid dose, etc.) in accordance with the needs of the individual. For example, a senior citizen leading a sedentary life may need higher daily doses than does a young person engaged in regular strenuous exercise (e.g., a weight lifter). Alternatively, the nutritional supplement of the present invention may be ingested on an as-needed basis at a dosage tailored to the individual's needs. Medical or nutritional counseling may be beneficial for arriving at a desirable or optimal dosage tailored to the individual's needs.

The combination of types of amino acids, mass ranges, and specific formulations have been selected to be synergistically balanced and of adequate quantity to achieve the desired physiological effect, namely, growth hormone release. Improper combinations of the amino acids may be ineffective. The component amino acids are synergistic in the sense that several of them when combined together, synergistically stimulate the release of human growth hormone. The combination was also chosen to reduce or inhibit chemical combination or reaction between the amino acids.

EXAMPLES

A cross-over, placebo controlled, double-blind study involved 16 healthy subjects [12 males, 4 females; 9 Caucasian, 6 African American, 1 other; mean age=32±14 years; body mass index=26.4±5.0 ranging from 19.1 to 36.8 kg/m$^2$]. Each subject reported to the Inpatient Unit on two occasions one week apart. After an overnight fast, subjects had an IV line placed and baseline bloods samples were drawn at −30, −15, and 0 minutes. Subjects were then asked to swallow the capsules of the test supplement or an identical looking placebo.

The administered supplement is a novel 2.9 g/dose blend of l-lysine HCl, l-arginine HCl, oxo-proline, N-acetyl-l-cysteine, l-glutamine, and schizonepeta (aerial parts) powder.

Blood was drawn at 15, 30, 60 and 90 and 120 minutes for assay. Human GH was measured at each time point using the Siemens Immulite 2000 (intra-assay CV was 3.72%, inter-assay CV was 5.70%, and the detection limit for GH was 0.05 ng/ml.

Mean growth hormone increased eight-fold over baseline (equivalent to 682%) after the supplement from 0.17 at baseline to 1.33 ng/ml at 120 minutes compared to a mean decrease of 52% after placebo from 0.93 to 0.45 ng/ml (FIG. 1). The mean change in GH levels from baseline to 120 minutes (GH at 120 minutes minus GH at 0 minutes), was 1.15 (95% CI: 0.17, 2.14) ng/ml after the supplement versus −0.48 (−1.47, 0.50) ng/ml after the placebo, demonstrating a statistically significant differential effect (P=0.01). After the supplement, the mean AUC for GH across 120 minutes was 20.43 (95% CI: 19.90, 20.95) ng/ml/min which was significantly higher (P=0.04) than placebo at 19.67 (18.74, 20.59) ng/ml/min. Overall, 120 minutes after taking the supplement, GH levels were significantly higher in both absolute levels and by AUC.

Mean levels of GH reached after the subcutaneous injection of 0.06 IU of HGH in the treatment of GH deficient subjects was 0.4 ng/ml, a value that was clearly in the range of values seen in our study with oral amino acids (Janssen Y J et al. *Br J Clin Pharmacol* 1999; 47:273-278).

The present study involved a broad range of ages and BMI's and included both genders. An additional advantage of this study of the amino-acid containing blend over previous hGH evaluations is that it contained a placebo control group and was randomized and double-blinded.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

We claim:

1. An oral nutritional supplement for increasing human growth hormone levels, comprising:
   3.44 mmol L-arginine;
   5.30 mmol Oxo-proline;
   8.21 mmol L-lysine;
   6.13 µmol N-acetyl L-cysteine;
   6.84 µmol L-glutamine; and
   0.50 mg Schizonepta (aerial parts) powder,
   wherein at least one of the L-arginine, the oxo-proline, the L-lysine, the cysteine, the N-acetyl L-cysteine, or the glutamine is in the form of non-toxic salts thereof, stable chelates thereof, active esters thereof, or mixtures thereof.

2. The supplement of claim 1, wherein the nutritional supplement is present in an amount of 2.9 grams.

3. The supplement of claim 1, wherein the nutritional supplement is in powder, tablet, capsule, liquid, or wafer form.

4. An oral nutritional supplement for increasing human growth hormone levels, comprising:
   725.50 mg L-arginine HCl;
   683.70 mg L-pyroglutamic acid;
   1499.30 mg L-lysine HCl;
   1.00 mg N-acetyl L-cysteine USP;
   1.00 mg L-glutamine; and
   0.50 mg Schizonepta (aerial parts) powder,
   wherein at least one of the L-arginine, the oxo-proline, the L-lysine, the cysteine, or the glutamine is in the form of non-toxic salts thereof, stable chelates thereof, active esters thereof, or mixtures thereof.

5. The supplement of claim 4, wherein the nutritional supplement is present in an amount of 2.9 grams.

6. The supplement of claim 4, wherein the nutritional supplement is in powder, tablet, capsule, liquid, or wafer form.

* * * * *